US009050450B2

(12) United States Patent
Hynynen et al.

(10) Patent No.: US 9,050,450 B2
(45) Date of Patent: Jun. 9, 2015

(54) ULTRASOUND THERAPY TRANSDUCER HEAD WITH TEMPERATIRE CONTROL STRUCTURE

(71) Applicant: Sunnybrook Health Sciences Centre, Toronto (CA)

(72) Inventors: Kullervo H. Hynynen, Toronto (CA); Junho Song, Toronto (CA)

(73) Assignee: Sunnybrook Health Sciences Centre, Toronto, Ontario (CA)

( * ) Notice: Subject to any disclaimer, the term of this patent is extended or adjusted under 35 U.S.C. 154(b) by 0 days.

(21) Appl. No.: 13/897,693

(22) Filed: May 20, 2013

(65) Prior Publication Data
US 2014/0163433 A1 Jun. 12, 2014

Related U.S. Application Data

(63) Continuation of application No. 12/397,984, filed on Mar. 4, 2009, now abandoned.

(60) Provisional application No. 61/095,171, filed on Sep. 8, 2008.

(51) Int. Cl.
| | |
|---|---|
| *A61N 7/02* | (2006.01) |
| *A61B 8/00* | (2006.01) |
| *B06B 3/00* | (2006.01) |
| *A61B 18/00* | (2006.01) |
| *A61N 7/00* | (2006.01) |

(52) U.S. Cl.
CPC . *A61N 7/02* (2013.01); *A61B 8/546* (2013.01); *A61B 2018/00011* (2013.01); *A61B 2018/00642* (2013.01); *A61N 2007/0078* (2013.01); *B06B 3/00* (2013.01)

(58) Field of Classification Search
CPC .......... A61B 2018/00011; A61B 2018/00642; A61B 8/546; A61N 2007/0078; A61N 7/02
See application file for complete search history.

(56) References Cited

U.S. PATENT DOCUMENTS

| | | | | | |
|---|---|---|---|---|---|
| 4,791,915 | A | * | 12/1988 | Barsotti et al. | 601/2 |
| 5,263,046 | A | * | 11/1993 | Vander Mey | 375/139 |
| 5,601,526 | A | * | 2/1997 | Chapelon et al. | 601/3 |
| 6,174,286 | B1 | * | 1/2001 | Ramamurthy et al. | 600/447 |
| 6,361,531 | B1 | * | 3/2002 | Hissong | 606/27 |
| 6,719,694 | B2 | * | 4/2004 | Weng et al. | 600/439 |
| 7,918,799 | B2 | * | 4/2011 | Haveri | 600/459 |
| 2006/0184072 | A1 | * | 8/2006 | Manna | 601/2 |

(Continued)

FOREIGN PATENT DOCUMENTS

JP 06125901 A * 5/1994

OTHER PUBLICATIONS

Machine Translation of JP 06-125901.*

(Continued)

*Primary Examiner* — Ruth S Smith
(74) *Attorney, Agent, or Firm* — Faegre Baker Daniels LLP (57) ABSTRACT

An ultrasound therapy transducer head comprises an ultrasound source emitting ultrasonic radiation, the ultrasound source comprising a plurality of transducer elements, integrated driving electronics coupled to the transducer elements, the electronics generating at least one output ultrasound waveform and driving at least some of the transducer elements independently based on the at least one output ultrasound waveform and temperature control structure providing cooling for the electronics.

53 Claims, 8 Drawing Sheets

(56) References Cited

U.S. PATENT DOCUMENTS

2007/0265560 A1    11/2007   Soltani et al.
2008/0183110 A1*    7/2008   Davenport et al. ............... 601/3
2008/0214966 A1     9/2008   Slayton et al.
2008/0269647 A1*   10/2008   Brunsveld Van Hulten ...... 601/2
2009/0099482 A1*    4/2009   Furuhata et al. .................. 601/2

OTHER PUBLICATIONS

Office Action dated Mar. 10, 2014 in corresponding Canadian Application No. 2,736,614.

* cited by examiner

ULTRASOUND THERAPY TRANSDUCER HEAD WITH TEMPERATIRE CONTROL STRUCTURE

CROSS-REFERENCE TO RELATED APPLICATION

This application is a continuation of U.S. application Ser. No. 12/397,984, filed Mar. 4, 2009, now abandoned, which claims the benefit of U.S. Provisional Application No. 61/095,171 filed on Sep. 8, 2008, entitled "Ultrasound Transducer Head and Ultrasound Therapy System Incorporating the Same", the contents of which are incorporated herein by reference.

FIELD OF THE INVENTION

The present invention relates generally to ultrasound therapy and in particular, to an ultrasound therapy transducer head and to an ultrasound therapy system incorporating the same.

BACKGROUND OF THE INVENTION

Ultrasound therapy uses high-frequency sound waves to produce heat that can reduce some types of acute and chronic pain and is often employed during physical, occupational or manipulation therapy to treat conditions such as musculoskeletal injuries, arthritis and fibromyalgia. Therapeutic ultrasound is typically delivered at frequencies between about 200 to about 10000 kHZ. Lowering the frequency of therapeutic ultrasound provides for deeper penetration of the sound waves. Sound waves penetrating the tissue of the subject cause molecules in the tissue to vibrate, producing heat and mechanical energy allowing for deep heating of tissues such as muscles, tendons, ligaments, joint capsules and bone. As is well known, therapeutic ultrasound differs from diagnostic ultrasound, which uses less-intense sound waves to create images of internal structure.

In the case of diagnostic ultrasound systems, compact electronics have been developed. For example, U.S. Pat. No. 5,924,993 to Hadjicostis et al. discloses an ultrasound mixed signal multiplexer/pre-amplifier application specific integrated circuit (ASIC) for supplying voltages to a group of transducer elements of an ultrasound array, receiving voltages from the same or another group of transducer elements of the ultrasound array, and amplifying the received voltages for transmission to external circuitry. The transmit and receive groups of transducer elements are shifted to provide accurate visual images with a minimal number of transmit and receive cycles.

U.S. Pat. No. 6,497,664 to Randall et al. discloses a medical diagnostic ultrasound receive beamformer including an upsampler upstream of both a time delay device and a summer, and a smoothing filter downstream of both the time delay device and the summer. The receive beamformer is automatically programmed into a gate array as a single-beam, dynamic-focus receive beamformer when the user selects B-mode and as a dual-beam, fixed-focus receive beamformer when the user selects color flow mode.

U.S. Pat. No. 6,969,352 to Chiang et al. discloses a hand-held ultrasound system including integrated electronics within an ergonomic housing. The integrated electronics include control circuitry, beamforming circuitry and transducer drive circuitry. The integrated electronics communicate with a host computer using an industry standard high speed serial bus. The ultrasound system is operable on a standard, commercially available, user computing device such as a personal computer (PC) without specific hardware modifications, and is adapted to interface with an external application without modification to the ultrasound system. This allows a user to gather ultrasonic data on the standard user computing device, and employ the data so gathered via the external application without requiring a custom system, expensive hardware modifications, or system rebuild. An integrated interface program allows such ultrasonic data to be invoked by a variety of external applications having access to the integrated interface program via a standard, predetermined platform such as Visual Basic or C++.

U.S. Pat. No. 7,169,108 to Little et al. discloses a continuous wave Doppler beam former application specific integrated circuit (CW-ASIC). The beam former may be a transmit or receive beam former. In one mode, the CW-ASIC is used in a diagnostic medical ultrasound system comprising a plurality of channels forming a CW analog receive path, wherein each channel is connected with a digital beam former. The plurality of channels are mixed down in quadrature to base band using a mixer and a local oscillator (LO) generator in quadrature. The outputs of the mixer are summed and wall/high pass filtered to provide a beam formed base band signal. A sub circuit provides a digital serial control function to interface to a real time control bus providing per channel enable/disable of the mixer and the LO generator, and LO delay as well as global local oscillator frequency select. The digital serial control function also has an external delay enable signal to start the LO generator and synchronize all the internal LO delays.

Although considerable attention has been paid to diagnostic ultrasound imaging systems, the same cannot be said as regards ultrasound therapy systems. The technologies described above relating to diagnostic ultrasound imaging systems are not applicable to therapeutic ultrasound delivery mainly due to the longer ultrasound bursts and higher time average power requried. As a result, there are still numerous barriers to the construction of fully electronically steerable, focused ultrasound devices for therapy including the number of transducer array elements, interconnects and driving and monitoring electronics that are required. As will be appreciated, further improvements in the design of ultrasound therapy systems are desired.

It is therefore an object of the present invention to provide a novel ultrasound therapy transducer head and ultrasound therapy system incorporating the same.

SUMMARY OF THE INVENTION

Accordingly, in one aspect there is provided an ultrasound therapy transducer head comprising an ultrasound source emitting ultrasonic radiation, said ultrasound source comprising a plurality of transducer elements; integrated driving electronics coupled to said transducer elements, said electronics generating at least one output ultrasound waveform and driving at least some of said transducer elements independently based on said at least one output ultrasound waveform; and temperature control structure providing cooling for said electronics.

In one embodiment, the electronics drive each of the transducer elements independently. The transducer elements are arranged in groups and wherein circuitry is provided for each group of transducer elements. The circuitry comprises digital and analog circuit components. For each group, the digital circuit comprises digital memory storing a digital waveform for each transducer element of the group and at least one digital to analog converter to convert each digital waveform output by the digital memory to an analog signal. The analog circuit comprises at least one amplification stage receiving the analog signal output of the at least one digital to analog converter and provides a variable driving signal to each transducer element of the group. The digital circuit and analog circuit for each group may be implemented on one integrated circuit chip or on separate integrated circuit chips.

According to another aspect there is provided an ultrasound therapy transducer head comprising an ultrasound source comprising at least one transducer element for generating an ultrasound beam; and an acoustic power sensing arrangement through which said ultrasound beam passes, said acoustic power sensing arrangement sensing the acoustic power of the ultrasound beam generated by said at least one transducer element.

In one embodiment, the ultrasound source comprises an array of transducer elements and wherein the acoustic power sensing arrangement senses the acoustic power of the ultrasound beam generated by each transducer element. The acoustic power sensing arrangement comprises a pressure sensitive layer and an electrode pair generally aligned with each transducer element. The electrodes of each electrode pair are positioned on opposite sides of the pressure sensitive layer. In one form, the pressure sensitive layer is a piezoelectric membrane and wherein each electrode pair develops a potential voltage between the electrodes thereof generally proportional to the power of the ultrasound beam generated by the associated transducer element. Readout circuitry electively reads out the potential voltages developed by the electrode pairs. Control circuitry communicates with the readout circuitry and the ultrasound source. The control circuitry provides feedback to the ultrasound source based on the potential voltages readout by the readout circuitry.

According to yet another aspect there is provided an ultrasound therapy transducer head comprising an ultrasound source comprising at least one transducer element for generating an ultrasound beam; and temperature control structure to control temperature within said ultrasound therapy transducer head.

In one embodiment, a coupling fluid reservoir containing coupling fluid is positioned adjacent the ultrasound source through which the ultrasound beam passes before exiting the transducer head. A heat exchanger cools the coupling fluid in response to at least one first sensor monitoring the temperature of the coupling fluid. The heat exchanger also cools the ultrasound source in response to at least one second sensor monitoring the temperature of the ultrasound source.

BRIEF DESCRIPTION OF THE DRAWINGS

Embodiments will now be described more fully with reference to the accompanying drawings in which.

DETAILED DESCRIPTION OF THE EMBODIMENTS

Figure 1:
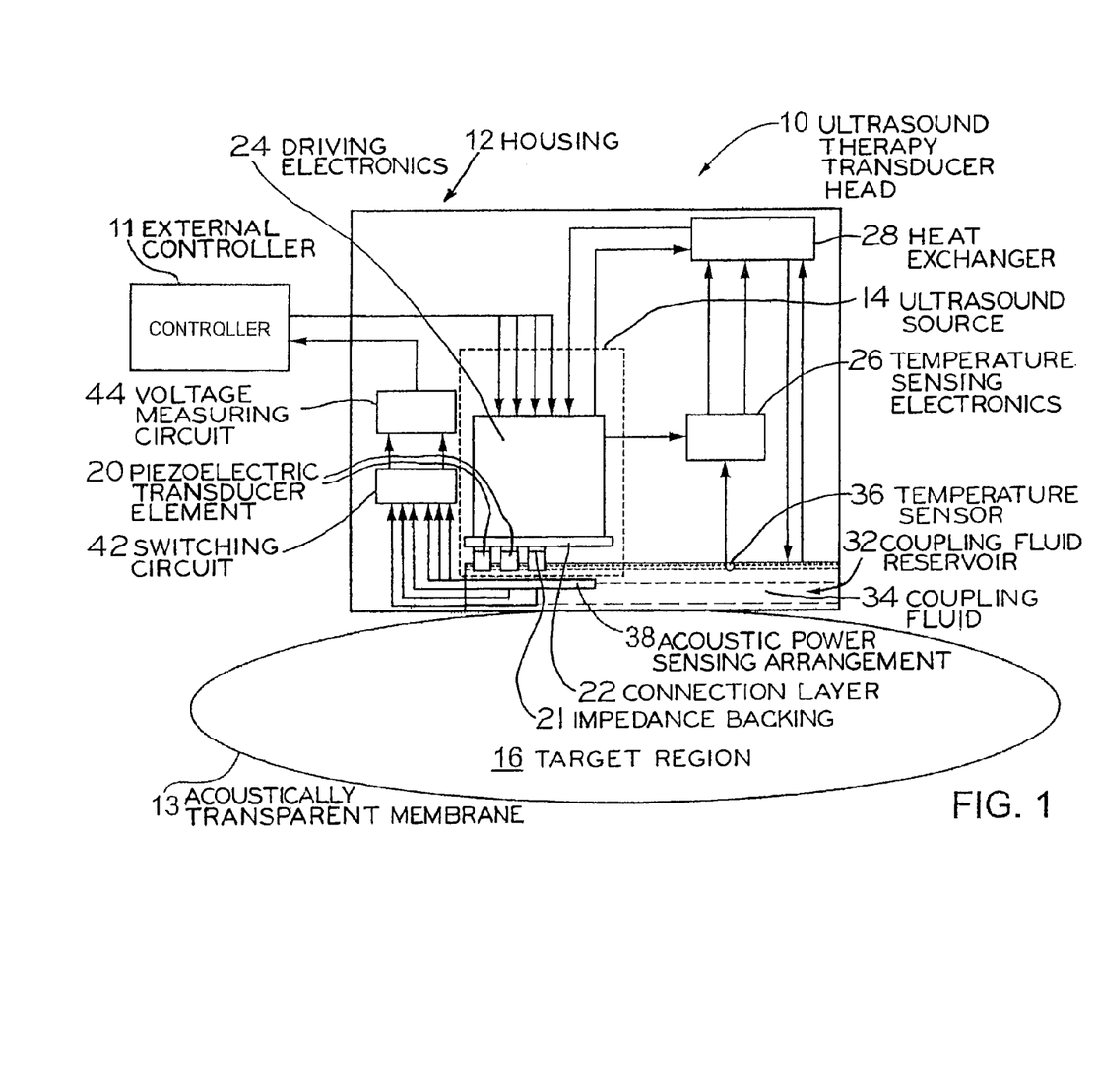
FIG. 1 is a schematic diagram of an ultrasound therapy system comprising an ultrasound transducer head and an external controller.
Figure 2:
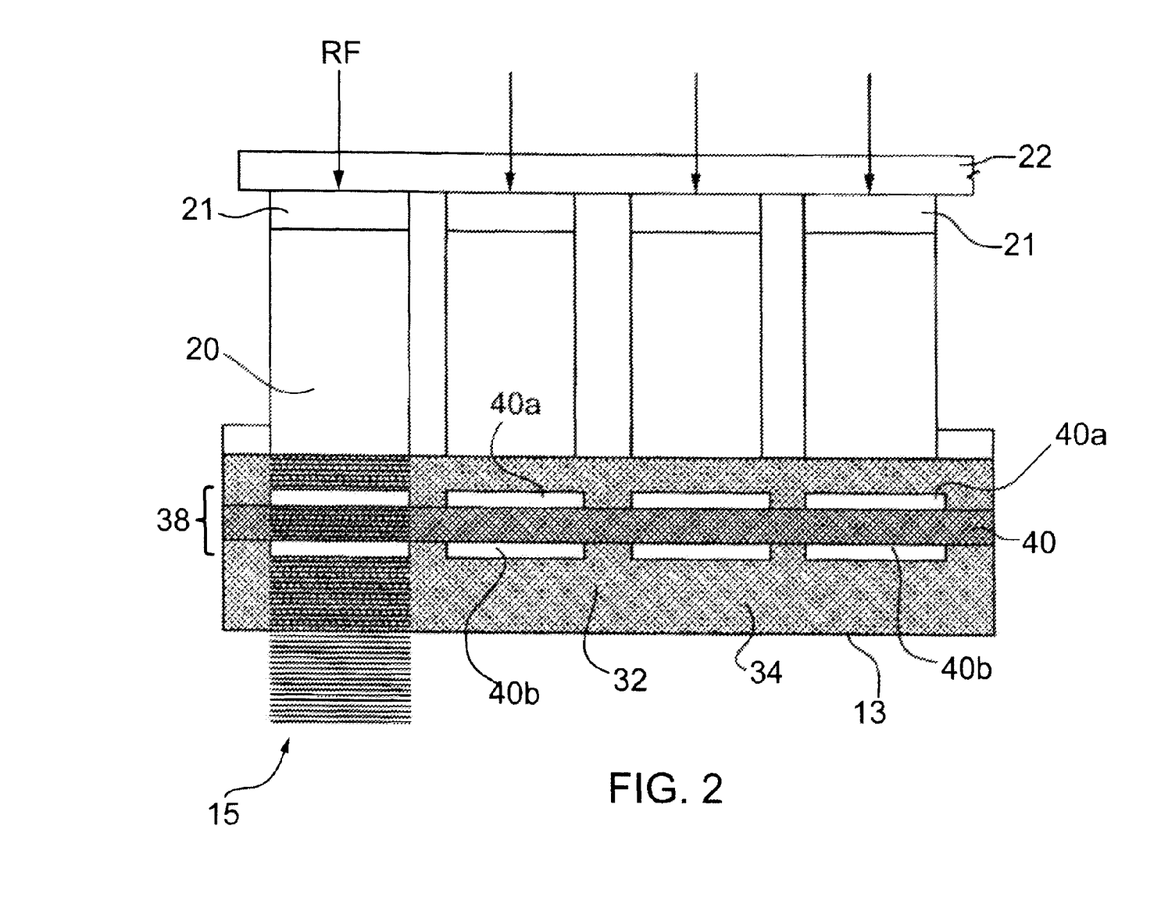
FIG. 2 is an enlarged schematic diagram of a portion of the ultrasound transducer head.

Turning now to FIGS. 1 and 2, a system for ultrasound therapy comprising an ultrasound therapy transducer head 10 coupled to an external controller 11 is shown. As can be seen, ultrasound transducer head 10 comprises a housing 12 that physically supports and protects internal ultrasound therapy source components. An acoustically transparent membrane 13 is provided at one end of the housing 12. An ultrasound source 14 that emits ultrasonic radiation 15 (i.e. acoustic signals or sound waves) that pass through the membrane 13 for application to a target region 16 of a subject selected for ultrasound therapy is mounted within the housing 12. The ultrasound source 14 comprises an array of piezoelectric transducer elements 20, only a small number of which are shown for illustrative purposes only. Each transducer element 20 has an impedance backing 21 thereon comprised of material with different impedance properties than the ultrasonic impendence properties of the associated transducer element 20.

A connection layer 22 in the form of a flex circuit or circuit board provides a mechanical mount for the transducer elements 20 and the impendance backing 21 as well as electrical connections between driving electronics 24 and the transducer elements 20. The driving electronics 24 also communicate with temperature sensing electronics 26 and a heat exchanger 28 disposed within the housing 20 as well as with the external controller 11. A coupling fluid reservoir 32 filled with a coupling fluid 34 is provided in the housing 12 adjacent the membrane 13. A temperature sensor 36 is positioned within the coupling fluid reservoir 32 and communicates with the temperature sensing electronics 26. The distal end of each transducer element 20 extends into the coupling fluid reservoir 32 and is immersed in the coupling fluid 34.

An acoustic power sensing arrangement 38 spaced from the array of transducer elements 20 is also disposed in the coupling fluid reservoir 32 and is positioned so that ultrasonic radiation emitted by the transducer elements 20 passes through the acoustic power sensing arrangement 38 before exiting the housing 12 via the membrane 13. The acoustic power sensing arrangement 38 is connected to a switching circuit 42 which in turn is connected to a voltage measuring circuit 44. The voltage measuring circuit 44 communicates with the external controller 11.

Figure 3:
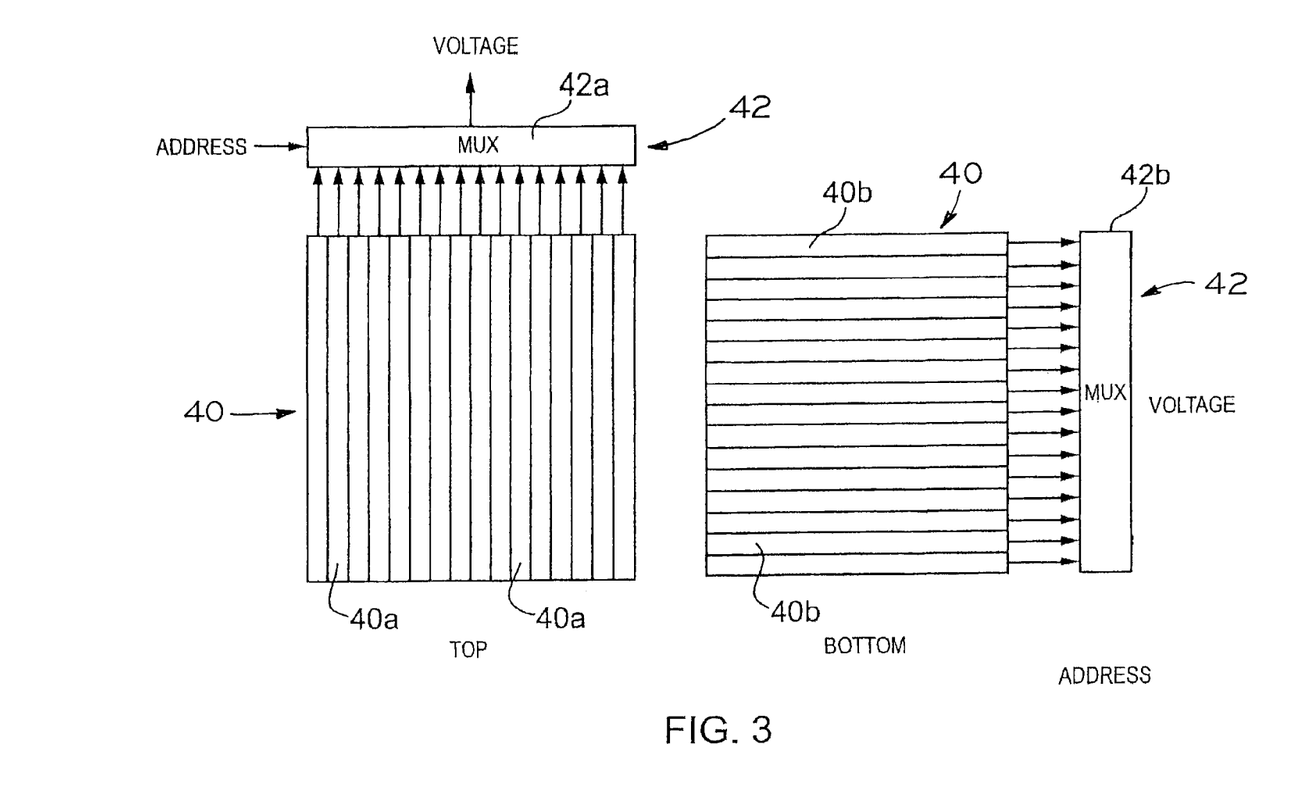
FIGS. 3 and 4 show an acoustic power sensing arrangement, a switching circuit and a voltage measuring circuit forming part of the ultrasound transducer head.
Figure 4:
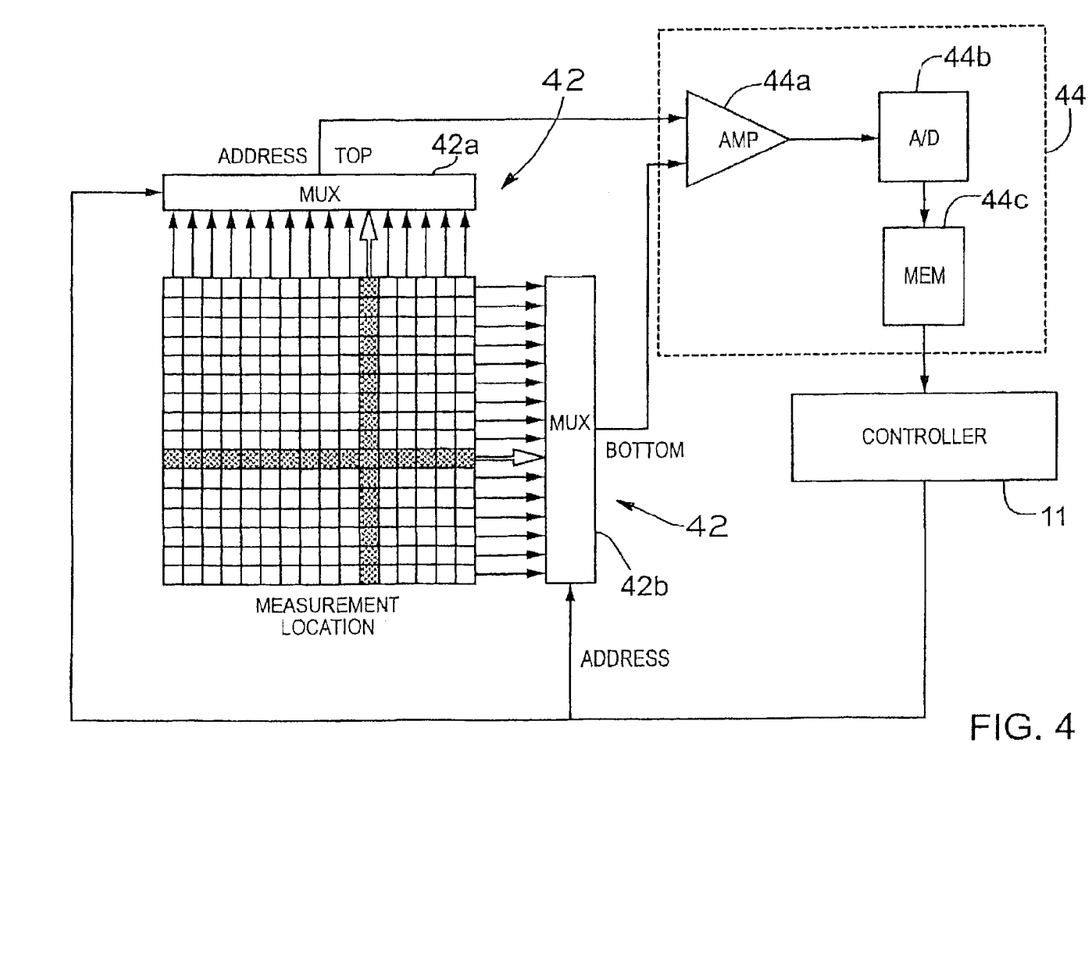

Turning now to FIGS. 3 and 4, the acoustic power sensing arrangement 38, switching circuit 42 (FIGS. 1, 2 and 4) and voltage measuring circuit 44 are better illustrated. In this embodiment, the acoustic power sensing arrangement 38 comprises a polarized piezoelectric membrane 40 (FIGS. 2 and 3) formed of polyvinylidene fluoride (PVDF). As is known, membranes of this nature are commonly used in hydrophones to measure ultrasound pressure waves in a medium such as water. A set of upper electrodes 40a in the form of generally parallel, laterally spaced strips and a set of lower electrodes 40b similarly in the form of generally parallel, laterally spaced strips are provided on opposite sides of the piezoelectric membrane 40. The electrode strips 40a of the upper set are generally orthogonal to the electrode strips 40b of the lower set. The upper electrode strips 40a and the lower electrode strips 40b overlap to form electrode pairs, with each electrode pair being aligned with a respective one of the transducer elements 20.

Referring to FIGS. 3 and 4, switching circuit 42 comprises a pair of multiplexers 42a and 42b. Each channel of multiplexer 42a is connected to a respective one of the upper electrode strips 40a and each channel of the multiplexer 42b is connected to a respective one of the lower electrode strips 40b. The multiplexers 42a and 42b receive address data from the external controller 11 allowing the voltage developed between each electrode pair to be readout.

As shown in FIG. 4, the voltage measuring circuit 44 comprises an amplifier 44a receiving input from the multiplexers 42a and 42b. The amplifier 44a provides output to an analog-to-digital converter 44b which in turn provides output to a memory 44c. Memory 44c communicates with the external controller 11.

Figure 5:
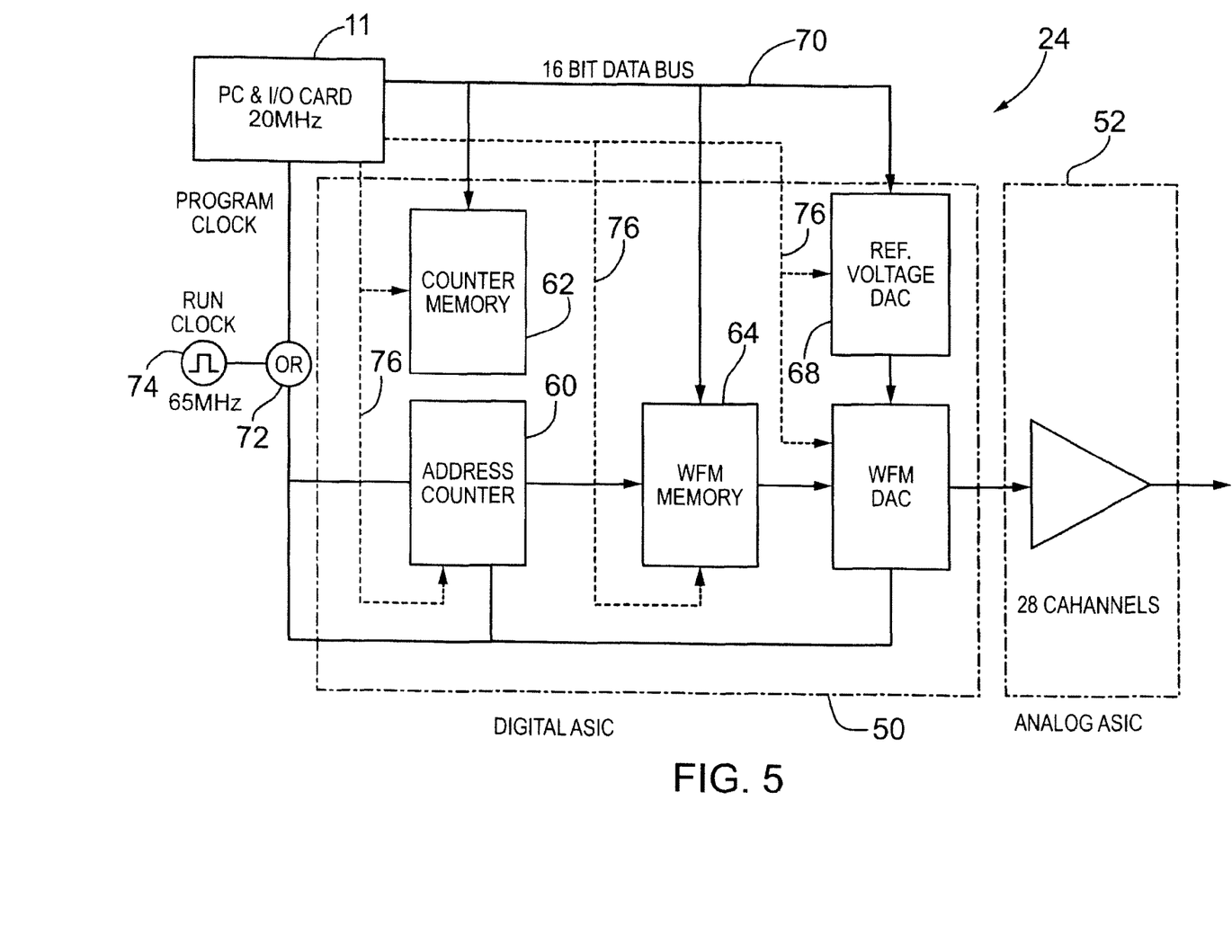
FIG. 5 is a schematic block diagram of electronics forming part of the ultrasound therapy system of FIG. 1.

In this embodiment, the transducer elements 20 are arranged in groups with each group comprising forty-eight (48) transducer elements 20 although this number may be increased or decreased as desired. The driving electronics 24 in this embodiment are formed of discrete components and comprise a digital circuit 50 and an analog circuit 52 for each group of transducer elements 20. FIG. 5 better illustrates one of the digital circuits 50 and one of the analog circuits 52. The digital circuit 50 comprises an address counter 60, an address counter memory 62, forty-eight (48) digital waveform memories 64 (only one of which is shown), forty-eight (48) waveform digital-to-analog converters (DACs) 66 (only one of which is shown) and a reference voltage DAC 68. The address counter memory 62, the digital waveform memories 64 and the reference voltage DAC 68 are connected to the external controller 11 via a 16-bit high speed data bus 70. The address counter 60 and the waveform DACs 66 are connected to the external controller 11 via OR logic 72 that is driven by a run clock 74. The address counter 60, address counter memory 62, digital waveform memories 64, waveform DACs 66 and reference voltage DAC 68 also communicate with the external controller 11 via control lines 76.

Each digital waveform memory 64 in this embodiment comprises 64K×10 bit static random access memory (RAM) that stores a digital waveform received from the external controller 11 via the high speed data bus 70. The digital values of the digital waveform at sampled time points are directly and serially loaded into each digital waveform memory 66 via the high speed data bus 70. The frequencies, amplitudes and phases of digital waveforms loaded into the digital waveform memories 66 by the external controller are selected so that the ultrasonic radiation 15 output by the ultrasound therapy transducer head 10 provides the desired therapeutic ultrasound to the subject. Parallel loading of the digital waveform into each digital waveform memory 64 is also feasible and will reduce the time required for the digital waveform loading procedure. The address counter memory 62 supplies rolling memory addresses to the address counter 60 at 20 MHz as the external controller 11 outputs data onto the high speed data bus 70 which in turn enables the digital waveform memories 64 so that the digital waveform data is stored in the proper digital waveform memories 64. Each digital waveform memory 64 is also addressed by the address counter 60 to ensure synchronization during output of digital waveforms by the digital waveform memories.

Once the digital waveform memories 64 have been loaded with the desired digital waveforms, each digital waveform memory is used to provide 10-bit digital waveform data to its associated waveform DAC 66 during the sonication. Each waveform DAC 66 converts the 10-bit digital waveform seen at its input to an analog signal with a dynamic range of 0 to 1 volt. The waveform DAC 66 is fast enough to allow adequate time resolution. During the sonication, the run clock 74 to the address counter 60 and the waveform DACs 66 is switched to a higher frequency oscillator (for example 65 MHz) to allow for adequate time resolution. Each waveform DAC 66 may also have additional features such as power down lines to allow individual channels to be disabled in the event of a channel down condition. Such a channel down condition occurs for example if the channel driving line becomes disconnected from its associated transducer element 20 or if the transducer element 20 is damaged. The reference voltage DAC 68 and its associated latch (not shown) are used to set the reference voltage for all the waveform DACs 66. This allows the total power level of the ultrasound source 14 to be adjusted in real time during sonication without requiring reloading of the digital waveform memories 66.

The analog circuit 52 comprises forty-eight (48) amplication circuits (only one of which is shown), each of which receives the analog signal output of an associated waveform DAC 66 and outputs a corresponding analog radio frequency (RF) signal that is applied to the channel driving line extending to an associated transducer element 20. The advantages of having each transducer element 20 connected to its own driving line include the reduction of the driving system size, cost, and power loss when the energy is transmitted from the driving electronics to the transducer element array.

Figure 6:
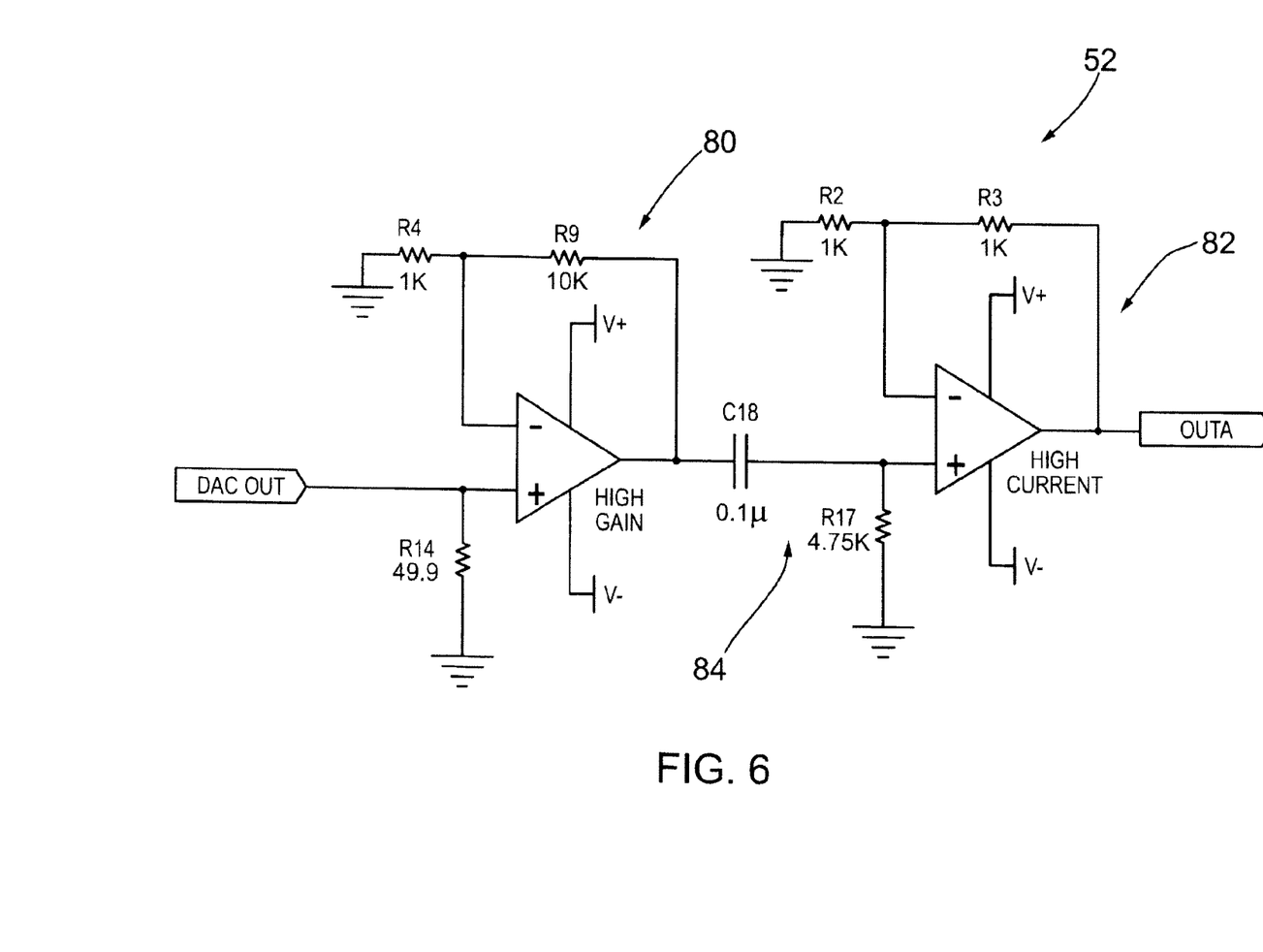
FIG. 6 is a circuit diagram of an analog amplifying stage forming part of the electronics of FIG. 5.

One of the amplification circuits is better illustrated in FIG. 6 and comprises a first Op-Amp stage 80 that provides a voltage gain to the analog signal, and a second Op-Amp stage 82 that provides a high current analog signal output. In this embodiment, the first Op-Amp stage 80 applies a voltage gain of eleven (11) to the DAC analog output signal augmenting the voltage swing from 0 to 11 volts. The Op-Amp stage 80 cuts out high frequencies and can be used to cut the quantization noise frequency. The signal output by the Op-Amp stage 80 is high-pass filtered with a first order resistor-capacitor (RC) circuit 84 to remove DC offset. The second Op-Amp stage 82 employs a high power Op-Amp to amplify the voltage, in this embodiment by a gain of two (2), and provide a high current analog output signal with a maximum peak-to-peak voltage swing of 22 volts.

Figure 7:
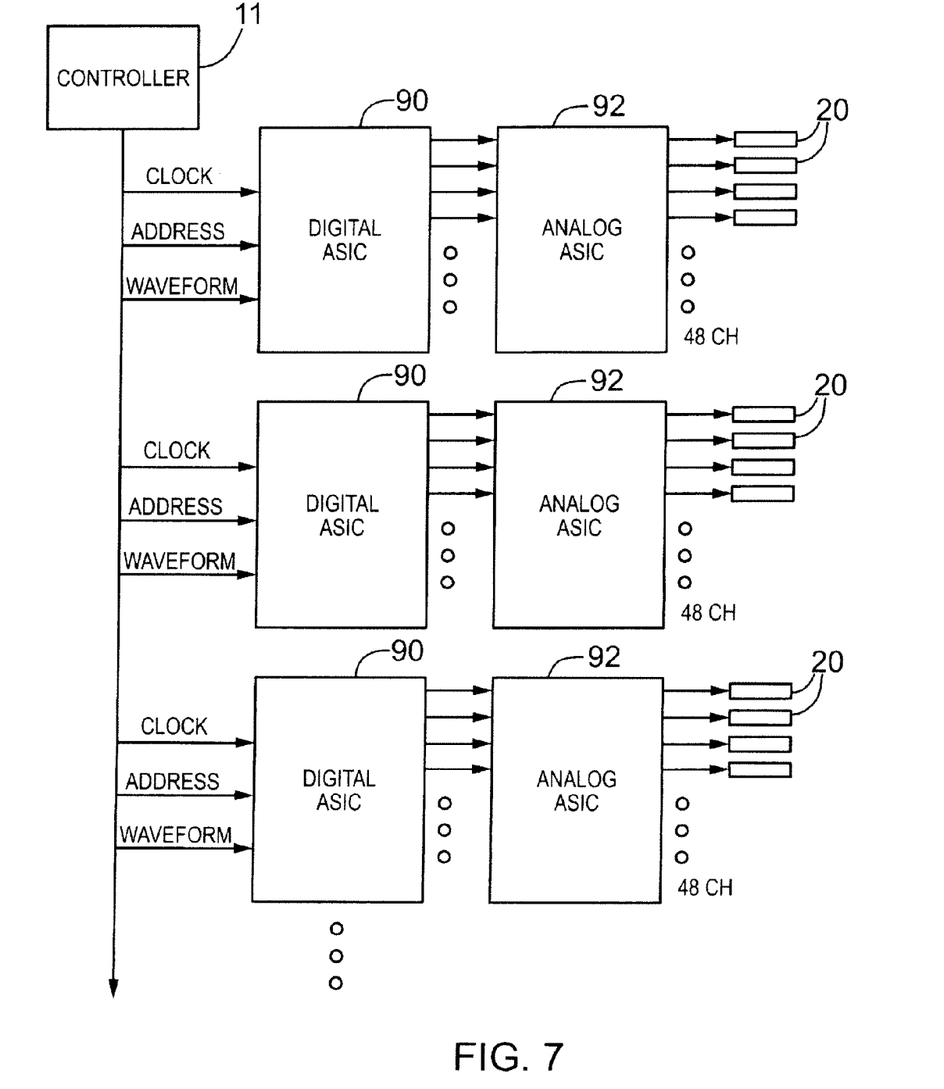
FIG. 7 is a schematic block diagram of one implementation of the electronics of FIG. 5.
Figure 8:
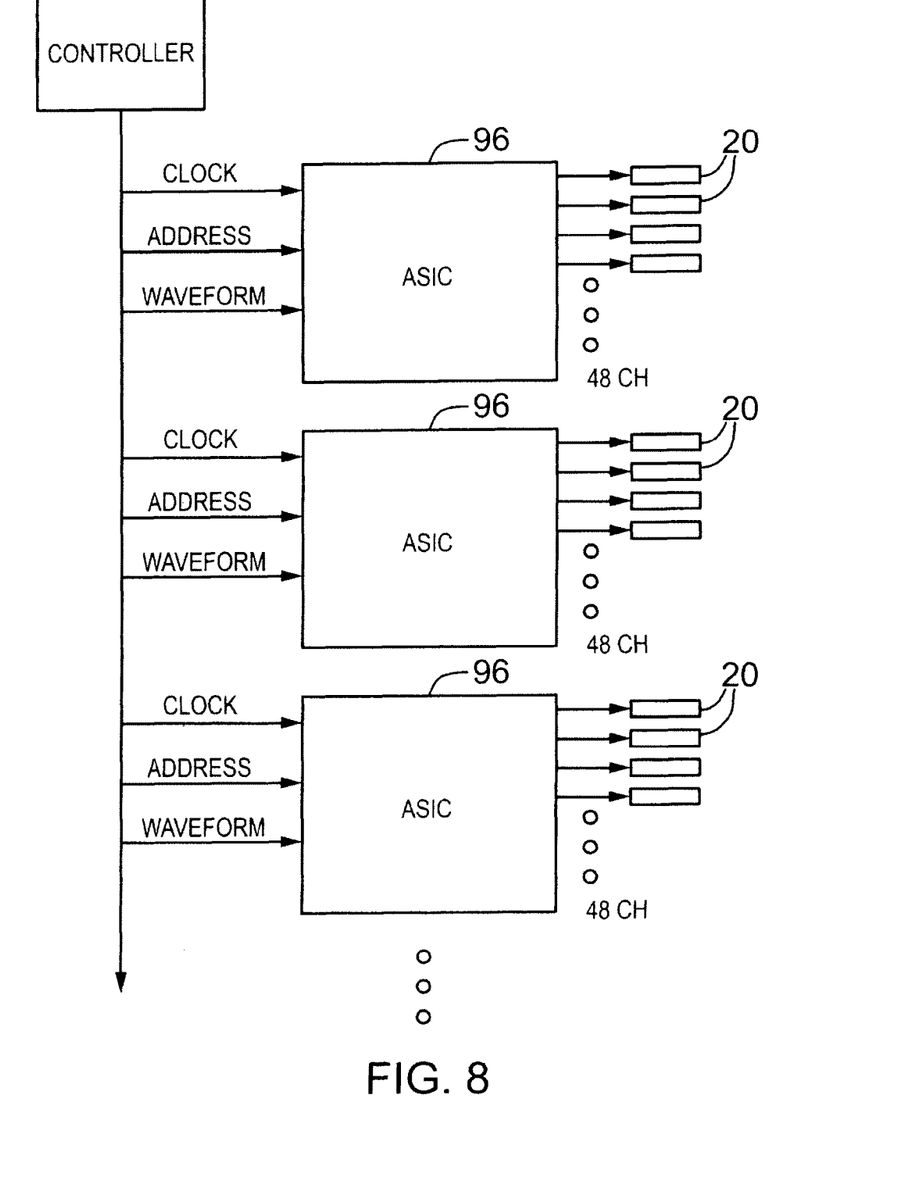
FIG. 8 is a schematic block diagram of another implementation of the electronics of FIG. 5.

The components shown in the shaded region of FIG. 5 represent the circuitry of the digital and analog circuits 50 and 52 that is repeated for each of the forty-eight (48) channels. The digital and analog circuits 50 and 52 can be constructed from discrete components or can be constructed using application specific integrated circuit (ASIC) chips. The digital circuit 50 can be combined on one ASIC chip 90 and the analog circuit 52 on another ASIC chip 92 as shown in FIG. 7. Alternatively, both the digital and analog circuits 50 and 52 can be combined on one chip 96 using a multiple-chip package (MCP) process as shown in FIG. 8. The Op-Amp stages 80 and 82 can be embedded in the module by integrating semiconductor intellectual property (SIP) blocks with ASIC/memories. The chip 90 or 96 may include a line that allows the status of the digital waveform memories 64 to be monitored to assure that each digital waveform is properly loaded.

The external controller 11 in this embodiment comprises a computing device such as for example, a Microsoft Windows based personal computer (PC) with a NI PCI-6534 (National Instruments, Austin, Tex.), an 80 Mbytes/second data transfer rate, and a 32-bit digital I/O board. The I/O board is controlled through a program executing on the computing device that uses the dynamic link library (DLL) supplied by the I/O board manufacturer. Binary data on thirty-two (32) data lines can be simultaneously transmitted for example at 20 MHz if an 80 Mbytes/s transfer rate is desired. Of the 32 data lines, 16 data lines form the high speed data bus 70 for transmitting digital waveform values, etc. to the driving electronics 24. The other 16 data lines are used as the control lines 76 for selecting, programming and manipulating different components of the driving electronics 24 and for higher level functions such as powering on and off individual digital circuits 50 and/or individual channels of the digital circuits 50.

The analog circuits 52 can be controlled by the external controller 11 for example through a parallel port. The external controller 11 can control electronic components of the ultrasound transducer head 10 via a serial port, universal serial bus (USB) or other suitable communications protocol. Each operation or instruction issued by the external controller 11 is coded with a specific 16-bit word that is used to directly control the appropriate component elements. 16-bit data arguments can be sent by the electronic components to the external controller 11 when required.

During operation, when the ultrasound transducer head 10 is conditioned to output ultrasonic radiation 15, the digital waveform data in each digital waveform memory 64 is output to its associated digital waveform DAC 66 and converted into an analog signal. Each analog signal is input to its associated amplification circuit resulting in an output RF signal that is fed to its associated transducer element 20. In response, each transducer element 20 outputs a beam of ultrasonic radiation corresponding to the digital waveform.

The ultrasound beam transmitted by each transducer element 20 passes through the acoustic power sensing arrangement 38 before exiting the transducer head 10 via the membrane 13. As each ultrasound beam passes through the acoustic power sensing arrangement, a varying voltage is formed in the piezoelectric membrane 40 between the electrode pair aligned with the transducer element 20 that is outputting the ultrasound beam as a result of the pressure variation created across the piezoelectric membrane 40. When the controller 11 addresses an electrode pair by enabling the multiplexers 42a and 42b connected to the upper and lower electrode strips 40a and 40b forming the electrode pair, the voltage across the piezoelectric membrane 40 between the electrode pair is sensed by the amplifier 44a. Amplifier 44a in turn outputs a voltage signal to the analog-to-digital converter 44b which converts the voltage signal to a digital value for storage in the memory 44c. Since the sensed voltage is proportional to the ultrasound pressure wave, the acoustic power delivered by each transducer element 20 can be measured. These measurements can be relative or they can be calibrated to provide absolute power measurements.

The generated voltage measurement signal output from the memory 44c by the voltage measuring circuit 44 is used by the external controller 11 to assure the proper operation of the transducer elements 20 and/or the driving electronics 24 allowing the ultrasonic radiation 15 output by the ultrasound therapy transducer head 10 to be precisely controlled. The generated voltage measurement signal may also be used to assure proper operation of the software executed by the external controller 11 during generation and loading of digital waveforms, to measure, display and/or control the amplitude of the emitted ultrasound beams, to measure, display and/or control the phase of the emitted ultrasound beams, and as a feedback signal to assure desired operation of the ultrasound therapy transducer head 10 such as by adjusting ultrasound beam amplitudes to stabilize power output.

The temperature sensing electronics 26 in this embodiment monitor the temperature of the coupling fluid 34 via temperature sensor 36 and the temperature of the driving electronics 24 via another temperature sensor (not shown) and provide output to the heat exchanger 28. In response to output from the temperature sensing electronics 26, the heat exchanger cools the coupling fluid 34 and/or the driving electronics 24 by circulating coolant through the housing 12 thereby to control temperature within the housing 12 and assure stable and reliable operation of the ultrasound therapy transducer head 10. The temperature sensing electronics 26 can signal the heat exchanger 28 so that it operates generally continuously to maintain a desired temperature within the housing or can cycle the heat exchanger 28. If desired, the temperature sensing electronics 26 may store temperature measurement and control data for transfer to the external controller 11.

If desired, the ultrasound therapy transducer head 10 may further comprise a controller to maintain and control the performance of the ultrasound therapy transducer head. Memory may be provided to store sonication, control and/or safety limit data as well as other data generated during ultrasound therapy transducer head monitoring. Additional electronics to enable automatic control and provide enhanced safety may also be included.

By integrating the array of transducer elements 20 with driving electronics 24 using custom integrated circuits in the transducer housing 12 and by using piezoelectric film technology integrated into the transducer housing 12 to monitor acoustic power output, the manufacturing costs of the ultrasound therapy transducer head 10 are significantly reduced providing for the ability to make ultrasound therapy systems that are not feasible with the current approaches.

Although the driving electronics 24 are described above as being connected to the array of transducer elements 20 via the connection layer 22, if desired, the driving electronics 24 may be directly connected to the transducer elements 20 obviating the need for the connection layer. If the connection layer does not provide the mechanical mounting then additional material is used to provide the mechanical mounting for the transducer elements 20. Also, if desired, the acoustic power sensing arrangement 38 can be positioned directly on the transducer element array face rather than being spaced from it as shown.

The form of the driving electronics 24 can of course vary from the examples described above and illustrated in the drawings. For example, if desired the amplification circuits may only include the high power Op-Amps. The analog output provided to the amplification circuits may be generated by individual waveform generators. In the example of FIG. 7, it is possible to realize only the digital circuits 50 in ASICs while using discrete components for the analog circuits 52.

Although embodiments have been described above with reference to the drawings, those of skill in the art will appreciate that variation and modifications may be made without departing from the spirit and scope thereof as defined by the appended claims.

What is claimed:

1. An ultrasound therapy transducer head comprising:
    an ultrasound source configured to emit ultrasonic radiation, said ultrasound source comprising a plurality of transducer elements;
    integrated driving electronics coupled to said transducer elements, said electronics configured to generate at least one output ultrasound waveform and drive at least some of said transducer elements independently based on said at least one output ultrasound waveform;
    a heat exchanger comprising coolant that is circulated within said transducer head to provide cooling at least for said electronics; and
    an acoustic power sensor adjacent said ultrasound source and spaced from said transducer elements so that ultrasound radiation emitted by said ultrasound source passes through said acoustic power sensor before exiting said transducer head, said acoustic power sensor configured to sense individually the acoustic power of ultrasound radiation emitted by each transducer element, and generate for each transducer element, an output representative of the acoustic power of ultrasound radiation emitted thereby.

2. An ultrasound therapy transducer head according to claim 1 wherein said electronics drives each of said transducer elements independently.

3. An ultrasound therapy transducer head according to claim 2 wherein said electronics comprise digital and analog circuit components.

4. An ultrasound therapy transducer head according to claim 3 wherein said transducer elements are arranged in groups and wherein circuitry is provided for each group of transducer elements, each said circuitry comprising digital and analog circuit components.

5. An ultrasound therapy transducer head according to claim 4 wherein each said circuitry comprises a digital circuit and an analog circuit.

6. An ultrasound therapy transducer head according to claim 5 wherein for each group, said digital circuit comprises digital memory storing a digital waveform for each transducer element of said group and at least one digital to analog converter to convert each digital waveform output by said digital memory to an analog signal and wherein said analog circuit comprises at least one amplification stage receiving the analog signal output of said at least one digital to analog converter and providing a variable driving signal to each transducer element of said group.

7. An ultrasound therapy transducer head according to claim 6 wherein said digital circuit comprises a digital memory and a digital to analog converter for each transducer element of said group and wherein said analog circuit comprises at least one amplification stage for each transducer element of said group.

8. An ultrasound therapy transducer head according to claim 7 wherein each analog circuit comprises a pair of serially connected amplification stages.

9. An ultrasound therapy transducer head according to claim 8 wherein each analog circuit further comprises a high-pass filter between said amplification stages.

10. An ultrasound therapy transducer head according to claim 9 wherein a first of said amplification stages applies a voltage gain to the analog signal output of the associated digital to analog converter and the second of said amplification stages generates a high current analog output signal based on the high-pass filtered output of the first of said amplification stages.

11. An ultrasound therapy transducer head according to claim 7 wherein for each group, said digital circuit further comprises addressing circuitry communicating with each of the digital memories, said addressing circuitry controlling output of the digital waveforms by said digital memories and the loading of the digital waveforms into the digital memories.

12. An ultrasound therapy transducer head according to claim 11 wherein said addressing circuitry comprises memory storing count values and an address counter responsive to said memory for conditioning said digital memories to output the digital waveforms.

13. An ultrasound therapy transducer head according to claim 11 wherein said digital circuit further comprises a reference voltage source communicating with each of the digital to analog converters.

14. An ultrasound therapy transducer head according to claim 7 wherein for each group, said digital circuit and analog circuit are implemented on at least one integrated circuit chip.

15. An ultrasound therapy transducer head according to claim 14 wherein said digital circuit and analog circuit are implemented on separate integrated circuit chips.

16. An ultrasound therapy transducer head according to claim 15 wherein each of said integrated circuit chips is an application specific integrated circuit chip.

17. An ultrasound therapy transducer head according to claim 14 wherein said digital circuit and analog circuit are implemented on a single integrated circuit chip.

18. An ultrasound therapy transducer head according to claim 17 wherein said single integrated circuit chip is formed using a multi-chip package process.

19. An ultrasound therapy transducer head according to claim 1 further comprising a coupling fluid reservoir containing coupling fluid positioned adjacent said ultrasound source through which emitted ultrasonic radiation passes before exiting said ultrasound therapy transducer head.

20. An ultrasound therapy transducer head according to claim 19 wherein said heat exchanger also cools said coupling fluid.

21. An ultrasound therapy transducer head according to claim 20 wherein a wall of said coupling fluid reservoir is an acoustically transparent membrane forming an external surface of said ultrasound therapy transducer head.

22. An ultrasound therapy transducer head according to claim 21 further comprising at least one sensor monitoring the temperature of said coupling fluid.

23. An ultrasound therapy transducer head according to claim 22 wherein said heat exchanger cools said coupling fluid in response to said at least one sensor.

24. An ultrasound therapy transducer head according to claim 1 wherein said acoustic power sensor comprises a pressure sensitive layer and an electrode pair generally aligned with each transducer element, the electrodes of each electrode pair being positioned on opposite sides of said pressure sensitive layer.

25. An ultrasound therapy transducer head according to claim 24 wherein said pressure sensitive layer is a piezoelectric membrane and wherein each electrode pair develops a potential voltage between the electrodes thereof generally proportional to the power of the ultrasonic radiation emitted by the associated transducer element.

26. An ultrasound therapy transducer head according to claim 25 further comprising readout circuitry for reading out the potential voltages developed by the electrode pairs.

27. An ultrasound therapy transducer head according to claim 26 wherein the readout circuitry selectively reads out the potential voltages developed by the electrode pairs.

28. An ultrasound therapy transducer head according to claim 27 further comprising control circuitry communicating with said readout circuitry and said electronics, said control circuitry providing feedback to said electronics based on the potential voltages readout by said readout circuitry.

29. An ultrasound therapy transducer head according to claim 28 wherein said heat exchanger provides cooling to said electronics based on said feedback.

30. An ultrasound therapy transducer head according to claim 24 further comprising a coupling fluid reservoir containing coupling fluid positioned adjacent said ultrasound source through which emitted ultrasonic radiation passes before exiting said transducer head.

31. An ultrasound therapy transducer head according to claim 30 wherein a wall of said coupling fluid reservoir is an acoustically transparent membrane forming an external surface of said ultrasound transducer head.

32. An ultrasound therapy transducer head according to claim 31 wherein said transducer elements and said acoustic power sensor are immersed in said coupling fluid.

33. An ultrasound therapy transducer head according to claim 32 further comprising readout circuitry for reading the sensed ultrasonic radiation acoustic power.

34. An ultrasound therapy transducer head according to claim 33 further comprising control circuitry communicating with said readout circuitry and said electronics, said control circuitry providing feedback to said electronics based on the sensed, ultrasonic radiation acoustic power readout by said readout circuitry.

35. An ultrasound therapy transducer head comprising:
an ultrasound source comprising an array of transducer elements configured to generate an ultrasound beam;
a coupling fluid reservoir positioned adjacent said ultrasound source and containing coupling fluid, the transducer elements of said array extending into said coupling fluid reservoir and being immersed in said coupling fluid;
an acoustic power sensor positioned in said coupling fluid reservoir at a location spaced from said transducer elements and immersed in said coupling fluid, the ultrasound beam generated by said ultrasound source passing through said coupling fluid and acoustic power sensor before exiting said transducer head, said acoustic power sensor configured to sense individually the acoustic power of the ultrasound beam generated by each transducer element; and
a single housing accommodating and physically supporting said ultrasound source, coupling fluid reservoir and acoustic power sensor.

36. An ultrasound therapy transducer head according to claim 35 wherein said acoustic power sensor comprises a pressure sensitive layer and an electrode pair generally aligned with each transducer element, the electrodes of each electrode pair being positioned on opposite sides of said pressure sensitive layer.

37. An ultrasound therapy transducer head according to claim 36 wherein said pressure sensitive layer is a piezoelectric membrane and wherein each electrode pair develops a potential voltage between the electrodes thereof generally proportional to the power of the ultrasound beam generated by the associated transducer element.

38. An ultrasound therapy transducer head according to claim 37 further comprising readout circuitry for reading out the potential voltages developed by the electrode pairs.

39. An ultrasound therapy transducer head according to claim 38 wherein the readout circuitry selectively reads out the potential voltages developed by the electrode pairs.

40. An ultrasound therapy transducer head according to claim 39 further comprising control circuitry communicating with said readout circuitry and said ultrasound source, said control circuitry providing feedback to said ultrasound source based on the potential voltages readout by said readout circuitry.

41. An ultrasound therapy transducer head according to claim 35 wherein a wall of said coupling fluid reservoir is an acoustically transparent membrane forming an external surface of said ultrasound transducer head.

42. An ultrasound therapy transducer head according to claim 41 further comprising readout circuitry for reading the sensed ultrasound beam powers.

43. An ultrasound therapy transducer head according to claim 42 further comprising control circuitry communicating with said readout circuitry and said ultrasound source, said control circuitry providing feedback to said ultrasound source based on the read ultrasound beam powers.

44. An ultrasound therapy transducer head according to claim 35 further comprising a heat exchanger for cooling said coupling fluid.

45. An ultrasound therapy transducer head according to claim 44 further comprising at least one first sensor monitoring the temperature of said coupling fluid.

46. An ultrasound therapy transducer head according to claim 45 wherein said heat exchanger cools said coupling fluid in response to said at least one first sensor.

47. An ultrasound therapy transducer head according to claim 46 further comprising at least one second sensor monitoring the temperature of said ultrasound source.

48. An ultrasound therapy transducer head according to claim 47 wherein said heat exchanger cools said ultrasound source in response said at least one second sensor.

49. An ultrasound therapy transducer head comprising:
an ultrasound source comprising an array of transducer elements configured to generate an ultrasound beam;
driving electronics coupled to said transducer elements, said electronics configured to generate at least one output ultrasound waveform and drive the transducer elements based on said at least one output ultrasound waveform;
a coupling fluid reservoir positioned adjacent said ultrasound source, said coupling fluid reservoir containing coupling fluid and having an acoustic power sensor therein that is immersed in said coupling fluid at a location spaced from said ultrasound source, said transducer elements extending into said coupling fluid reservoir and being immersed in said coupling fluid, the ultrasound beam generated by said ultrasound source passing through said coupling fluid and acoustic power sensor before exiting said transducer head, said acoustic power sensor configured to sense individually the acoustic power of the ultrasound beam generated by each transducer element;
a heat exchanger comprising coolant that is circulated within said transducer head to provide cooling for said electronics and said coupling fluid; and
a single housing accommodating and physically supporting said ultrasound source, driving electronics, coupling fluid reservoir, acoustic power sensor and heat exchanger.

50. An ultrasound therapy transducer head according to claim 49 further comprising at least one first sensor monitoring the temperature of said coupling fluid.

51. An ultrasound therapy transducer head according to claim 50 wherein said heat exchanger cools said coupling fluid in response to said at least one first sensor.

52. An ultrasound therapy transducer head according to claim 51 further comprising at least one second sensor monitoring the temperature of said ultrasound source.

53. An ultrasound therapy transducer head according to claim 52 wherein said heat exchanger cools said ultrasound source in response to said at least one second sensor.

* * * * *